US006039183A

United States Patent [19]
Rudnick et al.

[11] Patent Number: 6,039,183
[45] Date of Patent: Mar. 21, 2000

[54] BLISTER PACKAGE FOR IMPLANTABLE MEDICAL DEVICES

[75] Inventors: James J. Rudnick, Waldwick; Martin Golden, Highland Park, both of N.J.

[73] Assignee: Meadox Medicals, Inc., Oakland, N.J.

[21] Appl. No.: 09/146,653

[22] Filed: Sep. 3, 1998

Related U.S. Application Data

[60] Provisional application No. 60/057,983, Sep. 5, 1997.

[51] Int. Cl.[7] .................................................. B65D 85/08
[52] U.S. Cl. .......................... 206/570; 206/438; 206/486
[58] Field of Search ..................................... 206/438, 439, 206/363, 370, 570, 486, 488, 467, 469, 471

[56] References Cited

U.S. PATENT DOCUMENTS

| | | | |
|---|---|---|---|
| 4,697,703 | 10/1987 | Will . | |
| 5,405,005 | 4/1995 | White | 206/438 |
| 5,690,222 | 11/1997 | Peters | 206/438 X |

FOREIGN PATENT DOCUMENTS

| | | |
|---|---|---|
| 0 600 140 | 8/1994 | European Pat. Off. . |
| 2132587 | 11/1984 | United Kingdom . |

*Primary Examiner*—Jacob K. Ackun
*Attorney, Agent, or Firm*—Hoffmann & Baron, LLP

[57] ABSTRACT

A package assembly supports an implantable aortic arch graft in configuration for implantation. The aortic arch graft includes a main tube and plural branch tubes extending therefrom. A blister tray has a blister tray depression formed therein for accommodating the main tube and at least one of the branch tubes of the graft. A blister insert is insertably accommodating within the blister tray. The blister insert includes a blister insert depression formed in one surface thereof for accommodating another of the branch tubes of the graft. The blister insert maintains the branch tubes of the graft, supported by the blister tray, in spaced positioned from the branch tube supported by in the blister insert. A blister cover is removably disposed over the blister tray for covering the blister tray and enclosing the graft and the blister insert within the tray.

17 Claims, 6 Drawing Sheets

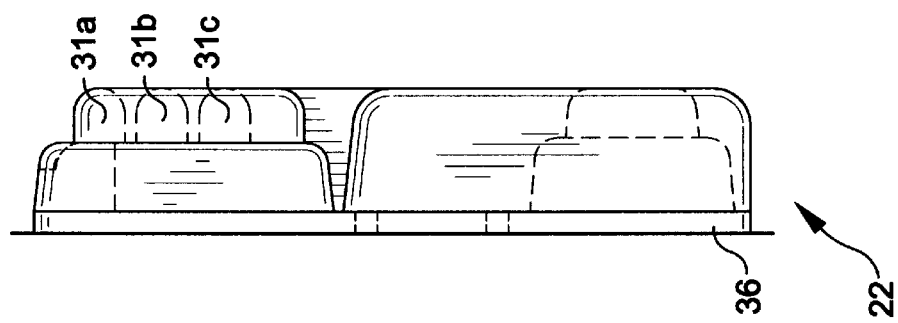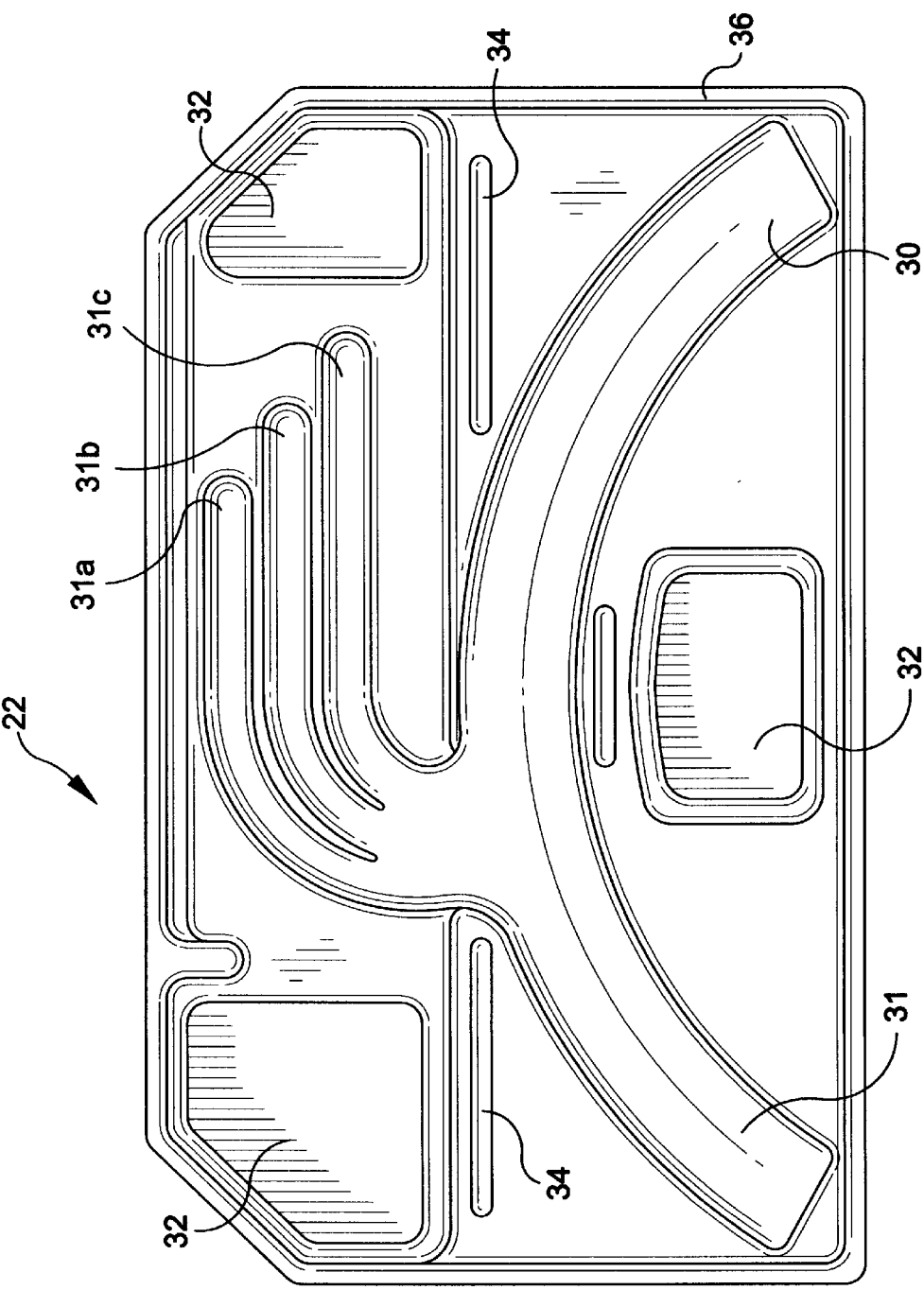

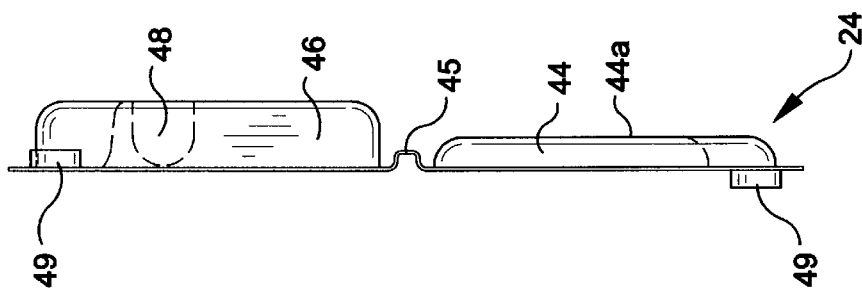
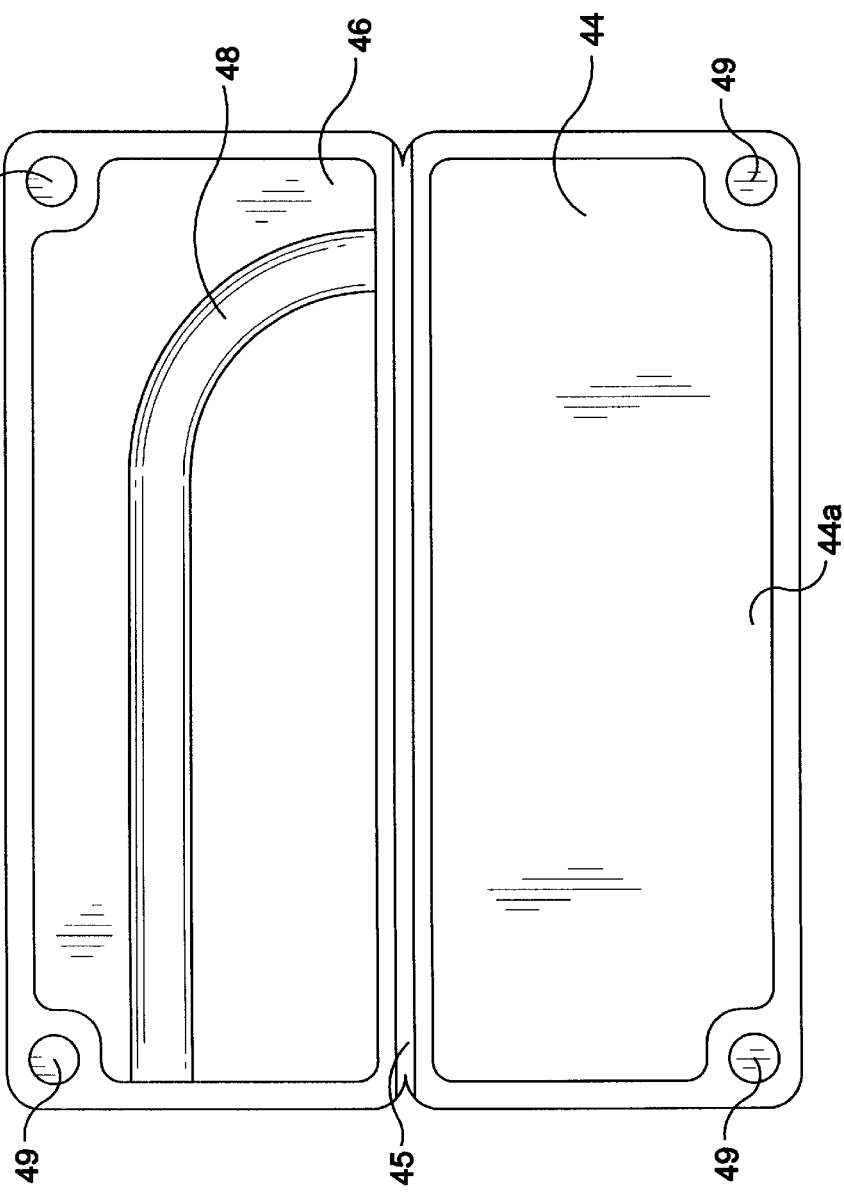

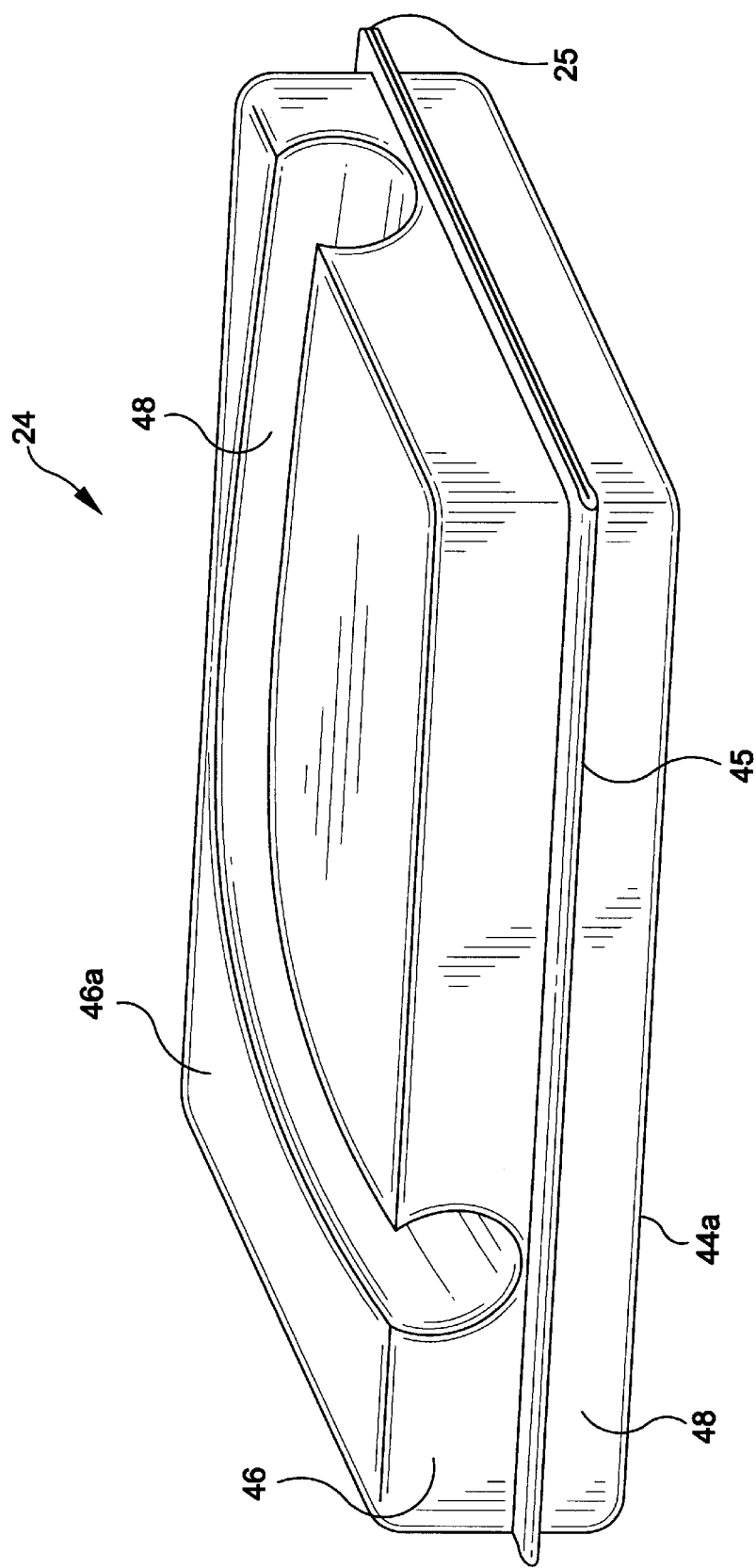

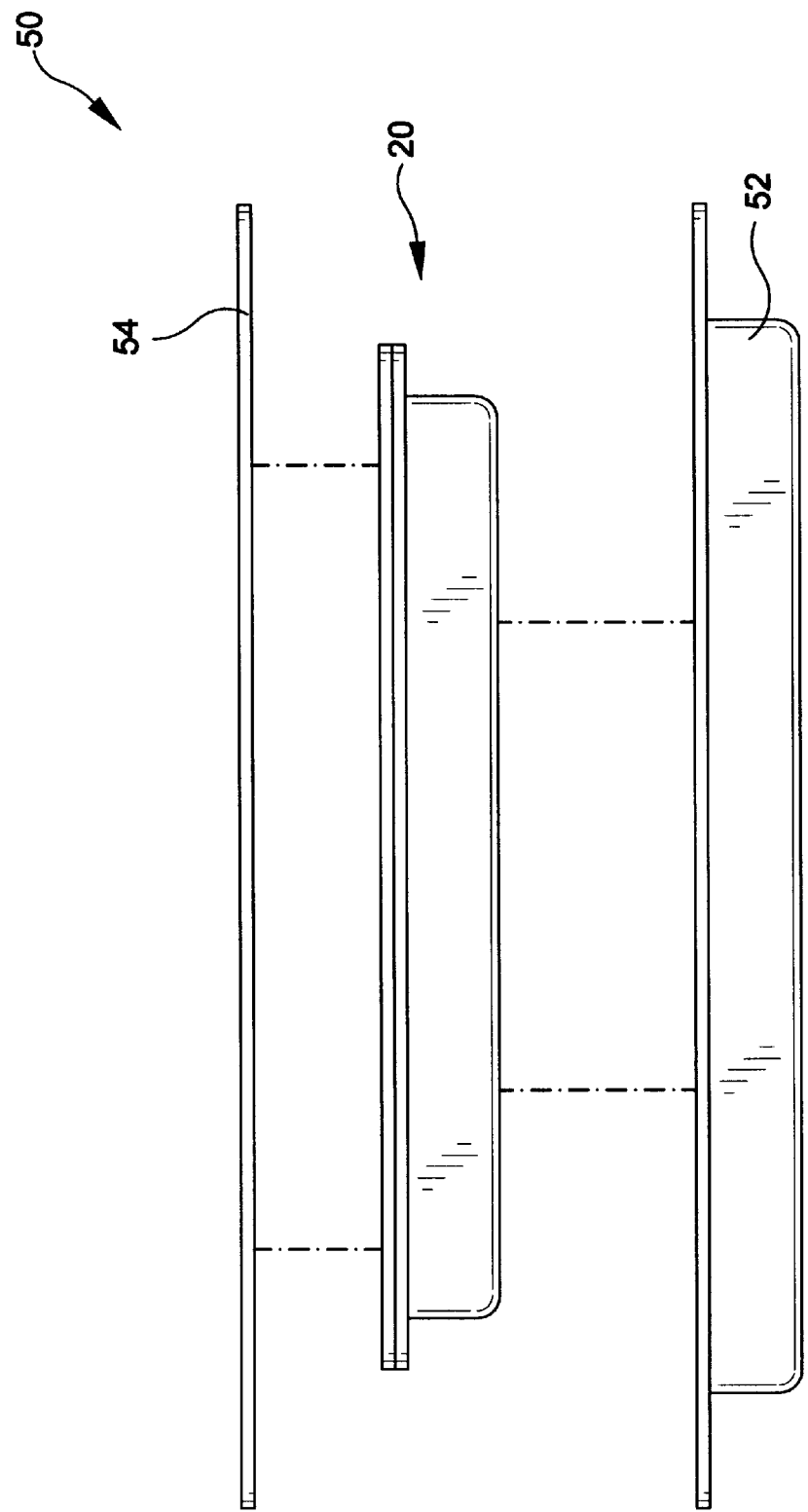

BLISTER PACKAGE FOR IMPLANTABLE MEDICAL DEVICES

This application claims the benefit of U.S. Provisional Application No. 60/057,983, filed on Sep. 5, 1997.

FIELD OF THE INVENTION

The present invention relates generally to a blister package used to support a medical device in a sterile environment. More particularly, the present invention relates to a blister package for supporting a vascular graft having complex shape in a protective sterile enclosure.

BACKGROUND OF THE INVENTION

In the field of medical devices, especially medical devices which are to be implanted in the body in surgical and nonsurgical procedures, such as implantable vascular grafts, it is necessary to provide a sterile protective environment for such grafts during shipping and storage prior to use. The use of blister packages which support vascular grafts in such a sterile environment is known in the art. Typical blister packages include blister trays, which are compression molded plastic members having specifically formed cavities or blister depressions formed therein which accommodate the vascular graft. These blister trays may be covered with a blister cover which is removably adhesively secured to the blister tray to enclose the vascular graft in the depression. As such, the interior of the blister package may be maintained in a sterile environment so that the vascular graft may be transported to the surgical site in a sterile condition. In use, the blister cover is peelably removed from the tray, rendering accessible the graft supported therein.

In order to provide enhanced sterility, the blister package itself may be enclosed in a second or outer blister package having a separate removable sealable blister cover positioned thereover. The outer blister package may also maintain a sterile environment interiorly thereof so that the inner blister package itself can be transported in a sterile condition.

For vascular grafts having relatively simple shapes, it is quite easy to form a blister package which accommodates the graft in a protective manner. Vascular grafts are typically elongate, cylindrical tubes which may include one or more branches at one end thereof. It is quite common to form the blister depressions in the blister tray to the precise shape of the particular graft which is to be supported therein. Furthermore, it is desirable to form the shape of the blister depression to mirror the shape and configuration of the graft as it is to be used or implanted. Such a configuration of the blister depression avoids kinking or bending of the graft during shipping and storage. The graft will thus be presented to the surgeon, prior to implantation, in the shape and configuration in which it is to be used. While it is relatively simple to provide blister depressions in a blister tray for grafts having simple configurations such as an elongate tube or a tube having one or more branches lying in a similar plane, such as is in the case of bifurcated grafts, it is more difficult to form a blister depression which will adequately accommodate grafts having more complex shapes.

One such graft is an aortic arch graft 10 shown in FIG. 1. Graft 10 includes an elongate main tube 12 and a plurality of aligned branch tubes 14 extending from the main tube 12 in parallel fashion. In certain situations where the aortic arch graft is designed to be temporarily connected to external devices, such as for example, a heart-lung machine, the graft 10 may include a lateral branch 16 extending from main tube 12 at a location spaced from the aligned branches 14.

Blister packages of the prior art have not been able to adequately accommodate such a complex-shaped aortic arch graft without sacrificing some degree of protection to the graft during shipment and long term storage.

It is therefore desirable to provide a blister package which is designed to accommodate a complex graft shape such as an aortic arch graft which protects the graft and maintains the graft in a sterile environment.

SUMMARY OF THE INVENTION

It is an object of the present invention to provide an improved package for supporting an implantable medical device.

It is a further object of the present invention to provide a blister package for supporting an aortic arch graft having a main tube and a plurality of branch tubes extending therefrom.

It is still a further object of the present invention to provide a blister package for supporting an aortic arch graft in a configuration generally ready for implantation.

In the efficient attainment of these and other objects, the present invention provides a package assembly for supporting an implantable aortic arch graft where the graft includes a main tube and plural branch tubes extending therefrom. The package assembly includes a blister tray having a blister depression formed therein. The blister depression accommodates the main tube and at least one of the branch tubes extending from the graft. A blister insert is insertably accommodated within the blister tray. The blister insert includes a first planar surface positionable adjacent the blister depression of the blister tray and a second planar surface in spaced opposition to the first planar surface. The second planar surface includes a depression formed therein for accommodating a further branch tube of the plural branch tubes and for maintaining spacial separation between the branch tubes in the blister tray and the further branch tube in the blister insert. A blister cover is removably positioned over the blister tray for covering the blister tray and enclosing the graft and the blister insert within the tray and maintaining the graft in a sterile environment.

As described by way of preferred embodiment herein, the covered blister tray may be enclosed within an outer package to maintain the covered blister tray in a sterile environment. Furthermore, the blister depressions formed in the blister tray and the blister insert are preferably of configuration which matches a configuration of the aortic arch graft during implantation.

BRIEF DESCRIPTION OF THE DRAWINGS

FIGS. 3 and 4 are top and side plan views respectively, of a blister tray of the package assembly of FIG. 2.

FIGS. 5 and 6 are top and side plan views respectively, of a blister insert of the package assembly of FIG. 1.

FIG. 7 shows the blister insert of FIGS. 5 and 6 in a folded configuration.

FIG. 8 is an exploded side elevational showing of the package assembly of the present invention enclosed in an outer blister package.

DETAILED DESCRIPTION OF THE PREFERRED EMBODIMENTS

Figure 1:
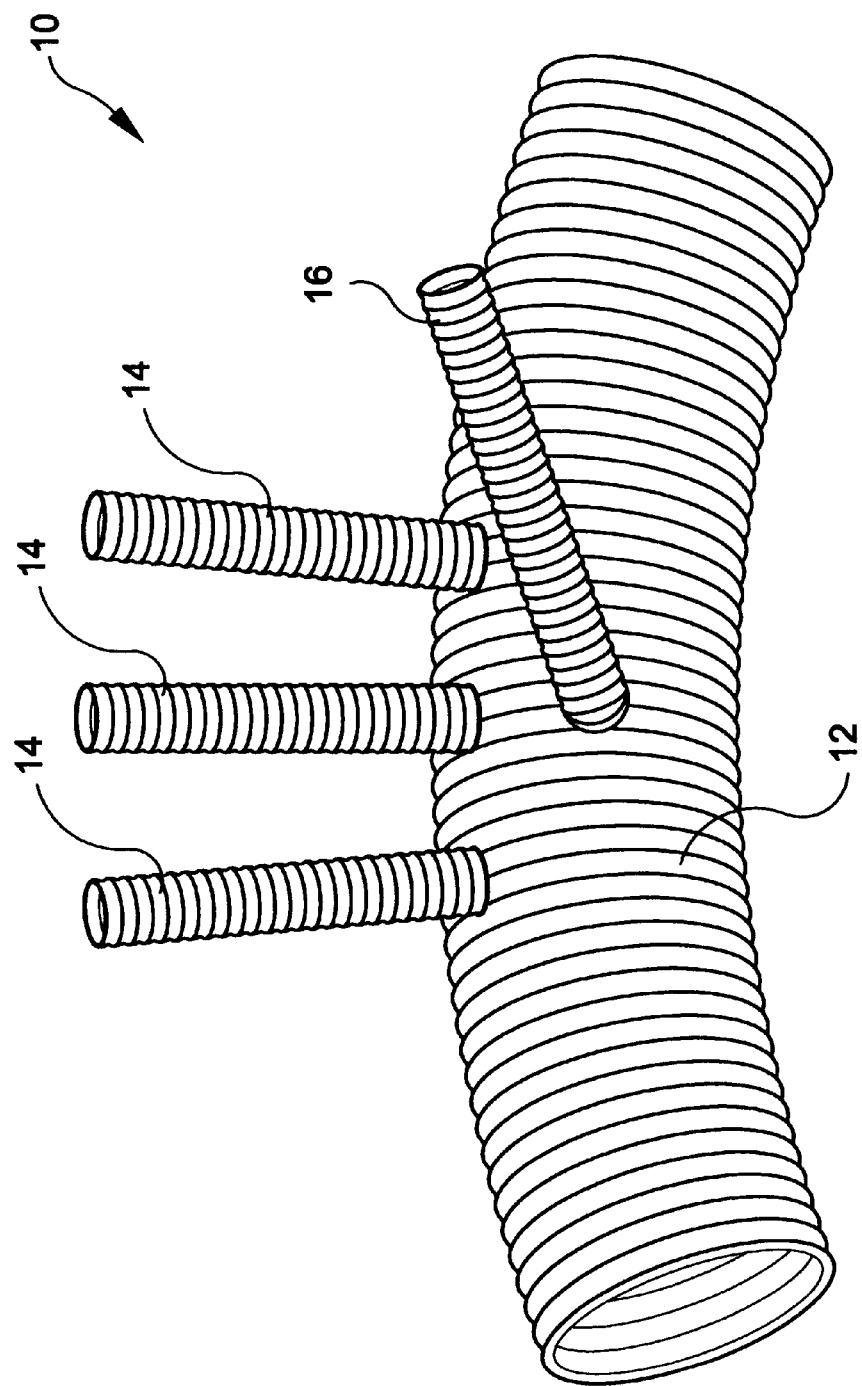
FIG. 1 is a perspective showing of implantable aortic arch graft which may be used in the package assembly of the present invention.
Figure 2:
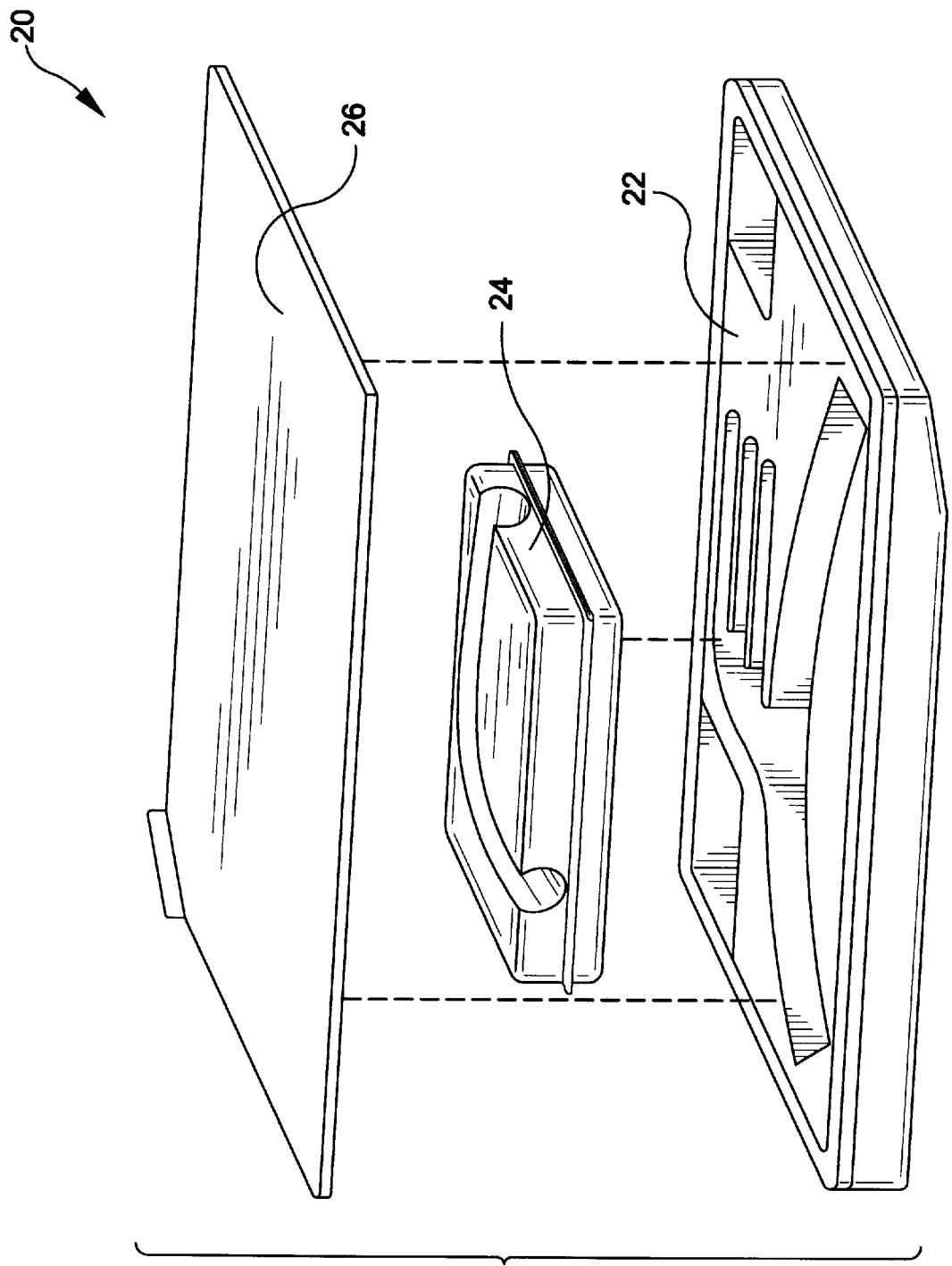
FIG. 2 is an exploded perspective view of the package assembly of the present invention.

The present invention provides a blister package assembly 20 shown in FIG. 2. Assembly 20 includes a blister tray 22, a blister insert 24 and a blister cover 26. The blister tray 22 may be formed of suitably formed die cut plastic such as polyethylene terephthalate (PET), including PETE and PETG, designed to support the aortic arch graft 10 of FIG. 1. Blister insert 24 may also be formed of a suitably formed die cut plastic such as PETE and is positioned to be supported over tray 22. The blister cover 26 which may be formed of a polyolefin such as TYVEK™ may be positioned over the blister tray to enclose the graft 10 therein. One surface of blister cover 26 may be adhesively coated to secure cover 26 to tray 22.

Referring more specifically to FIGS. 3 and 4, blister tray 22 is generally an open-ended rectangular member having a major blister depression 30 formed therein. Blister depression 30 takes the shape of the aortic arch graft 10 shown in FIG. 1, having a central area 31 configured to accommodate the main tube 12 and aligned branch areas 31a, 31b, and 31c in communication with central area 31 to accommodate branch tubes 14. It is noted that blister depression 30 is sized and shaped to uniquely accommodate aortic arch graft 12 in a position generally conforming to that at which it is implanted. The configuration of blister depression 30 is such that aortic arch graft 10 may be maintained in the blister depression without bending or kinking. Also, the blister depression 30 maintains each of the branches 14 in spaced non-contacting relationship in the blister tray.

In addition to main depression 30 used to accommodate aortic arch graft, blister tray 22 may also include plural additional depressions 32 which are provided for structural stability of the blister tray. Further, blister tray 22 also includes a plurality of standoff locations 34 extending from the bottom of the blister tray. Each standoff location 34 together with a perimetrical rim 36 of blister tray 32 provide a surface to which the adhesive coated blister cover 26 may be applied.

Referring now to FIGS. 5, 6 and 7, blister insert 24 may be described. Blister insert 24 is generally a rectangular member having a pair of blister cavities 44 and 46 formed on each side of a fold line 45. Blister cavity 44 includes a generally continuous first planar bottom surface 44a. Blister cavity 46 also includes a second planar bottom surface 46a which includes an elongate curved reverse blister depression 48 formed thereon. Reverse blister depression 48 opens outwardly to the planar surface 46a and is configured in a shape to conform to the lateral branch 16 (FIG. 1) when in use. Reverse blister depression 48 is open at each end to side surfaces of cavity 46. Blister insert 24 may be folded about a fold line 45 into the configuration shown generally in FIG. 7.

In order to maintain the blister insert in the folded configuration, a plurality of cooperating detent members 49 are provided at the corners thereof. Opposed detent members 49 interlock when the blister insert 24 is folded about fold line 45 so as to maintain the blister insert in the folded configuration. In the folded configuration shown in FIG. 7, blister insert 24 presents bottom surface 44a as a flat uniformly smooth member on one side and presents reverse blister depression 48 for the accommodation of lateral branch 16 on the other side thereof formed by planar surface 46a. Thus, as shown in FIG. 7, reverse blister depression 48 is maintained in spaced opposition to planar bottom surface 44a.

Having described the components of the blister package assembly 20 of the present invention, its use and operation may be further described with specific reference to FIGS. 1, 2, 3, 5 and 7. Aortic arch graft 10 is positioned within major depression 30 of blister tray 22. Main tubular member 12 lies within the curved central area 31 of blister depression 30. The aligned extending branches 14 are positioned in each of the associated branch areas 31a, 31b, and 31c. The lateral branch 16 is held away from the blister tray 22 so that blister insert 24, in the folded condition shown in FIG. 7, may be inserted into blister tray 22. Blister insert 24 is inserted in a position where the generally planar bottom surface 44a is positioned directly over the branches 14 supported in branch areas 31a, 31b and 31c. Thus, a smooth surface is presented directly adjacent the graft branches 14. Such positioning of a smooth surface there adjacent reduces any incidence of damage to the branches 14 when coming in contact with the blister insert 24 during shipment and storage. Furthermore, blister insert 24 is positioned within blister tray 22 in a position where the fold line 45 is positioned adjacent the central area 31 of blister depression 30 at the region of branches 14 and lateral branch 16. In this manner, the smoother folded side rather than the die cut edges 25 of the blister insert 24 are positioned adjacent the main body 12 and the region of attachment of branches 14 and lateral branch 16 to graft 10. Again, maintaining the die cut edges 25 of blister insert 24 away from the graft 10 during shipment and storage protects the graft and prevents damage thereto.

Once the graft is supported in blister tray 22 in the manner described above and the blister insert 24 is properly inserted, the lateral branch 16 is positioned in reverse blister depression 48. The reverse blister depression 48 has a length sufficient to fully accommodate a range of lengths of lateral branch 16. So positioned, the blister insert 24 spaces and separates the lateral branch 16 from aligned branches 14 of graft 10.

Subsequent to such positioning, the blister tray 22 may be covered with blister cover 26. An appropriate application of heat and pressure is used to secure the blister cover 26 to the blister tray 24. Adhesive engagement is established between blister cover 26 and the perimetrical rim 36 of blister tray 22 and the surfaces provided by standoffs 34. This prevents the blister cover 26 from becoming inadvertently dislodged from the blister tray 22 or from separating therefrom. The blister insert 24 is loosely accommodated in tray 24. This loose accommodation allows blister tray 24 to "float" within the tray 24. This prevents the insert 24 from being held in a non-desirable position. However, the insert 24 is adequately supported in the tray 22 by cover 26.

As is shown in FIG. 8, it is further contemplated, that blister package assembly 20 may be further enclosed in an outer blister package 50 to enhance further protection and sterility. Such outer blister package 50 includes an outer blister tray 52 which is designed to accommodate blister package assembly 20. An outer blister cover 54 may be used to fully enclose blister assembly 20 in outer blister tray 52.

It can be appreciated that the present invention allows the protective accommodation of a complex graft configuration having a plurality of branches where the branches extend in different planar orientations from the main body of the graft.

Various changes and modifications can be made to the present invention. It is intended that all such changes and modifications come within the scope of the invention as set forth in the following claims.

What is claimed is:

1. A packaged implantable device comprising:
   an implantable aortic arch graft having a main tube and at least one branch tube extending therefrom;
   a blister tray having a blister tray depression formed therein for accommodating said main tube;

a blister insert positionable within said blister tray, said blister insert having formed therein an insert depression for accommodating therein said at least one branch tube and for maintaining spaced separation between said at least one branch tube and said main tube; and a blister cover removably disposed over said blister tray for covering said blister tray and enclosing said graft and said blister insert within said tray for maintaining said graft in a sterile environment.

2. A packaged implantable device of claim 1 further including an outer package for enclosing said covered blister tray and maintaining said covered blister tray in a sterile environment.

3. A packaged implantable device of claim 2 wherein said outer package includes:

an outer blister tray for accommodating said covered blister tray; and an outer blister cover removably securable to said outer blister tray for enclosing said covered blister tray.

4. A packaged implantable device of claim 1 wherein said blister depression of said blister tray includes a main tube depression said at least one plural branch tube depression in communication with said main tube depression.

5. A packaged implantable device of claim 4 wherein said blister tray includes plural spaced apart branch tube depressions in communication with said main tube depression for accommodating plural branch tubes of said graft in non-contacting relationship.

6. A packaged implantable device of claim 5 wherein each of said main tube depression and said plural branch tube depressions include a curved configuration.

7. A packaged implantable device of claim 1 wherein said blister tray includes a perimetrical rim extending therearound for supporting said blister cover.

8. A packaged implantable device of claim 7 wherein said blister cover is secured to said perimetrical rim of said blister tray with an adhesive.

9. A packaged implantable device of claim 1 wherein said blister insert is a generally planar member being foldable about a central fold line into a folded configuration, said blister insert defining said opposed first and second planar surfaces in said folded configuration.

10. A packaged implantable device of claim 9 wherein said generally planar member of said blister insert includes a blister cavity formed on each side of said folded line, said blister cavity on one side of said fold line forming said first planar surface and said blister cavity on said other side of said fold line forming said insert depression.

11. A kit of parts comprising:

an aortic arch graft having a main tube and a plurality of branch tubes extending therefrom; and a package assembly adapted to support said aortic arch graft, said package assembly including a blister tray having a blister depression adapted to support said main tube and a blister insert having an insert depression adapted to support at least one of said branch tubes, said blister insert being supportable within said blister tray so as to provide spacial separation between said main tube and said at least one branch tube.

12. A kit of parts of claim 11 further comprising:

a blister cover adapted to be removably positioned over said blister tray for covering said blister tray and enclosing said graft and said blister insert within said tray.

13. A kit of parts of claim 12 further comprising:

an outer package adapted for enclosing said covered blister tray.

14. A kit of parts of claim 13 wherein said outer package further includes an outer blister tray adapted to accommodate said covered blister tray and an outer blister cover adapted for covering said covered blister tray.

15. A method of packaging an aortic arch graft having a main tube and a plurality of branch tubes extending therefrom comprising the steps of:

providing a blister tray having a blister depression formed therein;

inserting said main tube of said graft in said blister depression;

providing a blister insert having an insert depression formed therein;

inserting at least one of said branch tubes of said graft in said insert depression; and positioning said blister insert within said blister tray over said main tube so as to spacially separate said at least one branch tube from said main tube.

16. A method of claim 15 further comprising the steps of:

providing a blister cover;

positioning said blister cover over said blister tray for enclosing said graft and said blister insert with said tray.

17. A method of claim 16 further comprising the steps of:

enclosing said covered blister tray in an outer package.

* * * * *